United States Patent [19]

Ishiguro

[11] 4,148,881
[45] Apr. 10, 1979

[54] MITICIDAL COMPOSITIONS COMPRISING ANTIBIOTIC K-41

[75] Inventor: Takeo Ishiguro, Kusatsu, Japan
[73] Assignee: Shionogi & Co., Ltd., Osaka, Japan
[21] Appl. No.: 818,098
[22] Filed: Jul. 21, 1977
[30] Foreign Application Priority Data
  Aug. 6, 1976 [JP] Japan .................................. 51/94128
[51] Int. Cl.² ............................................. A01N 9/00
[52] U.S. Cl. .................................................. 424/120
[58] Field of Search ........................................ 424/120

[56] References Cited
PUBLICATIONS
Tsuji et al., The Journal of Antibiotics, vol. 29, No. 1, pp. 10-14 (1976).

Primary Examiner—Allen J. Robinson
Attorney, Agent, or Firm—Wenderoth, Lind & Ponack

[57] ABSTRACT

This invention relates to miticidal compositions comprising antibiotic K-41 having a combating effect against a broad variety of mites.

5 Claims, No Drawings

MITICIDAL COMPOSITIONS COMPRISING ANTIBIOTIC K-41

This invention relates to miticidal compositions comprising antibiotic K-41 as an active ingredient. Further, it relates to a process for preparing the same and a method of using the said compositions to protect plants from attack of mites.

Mites have caused an annoying problem in crops, fruit trees and domestic animals. Particularly, they heavily damage various fruit trees such as apple, orange, grape and pear trees, vegetables such as eggplants and cucumbers, and flowering horticultural plants such as carnations and the like. The difficulty in controlling mites consists in the ease with which they acquire resistance. Thus, a new type of miticide has been desired. This invention provides new miticidal compositions comprising an antibiotic.

The antibiotic K-41 contained in the said compositions is produced by Streptomyces sp. K-41 (deposited at American Type Culture Collection under accession No. 31,227 and at Fermentation Research Institute, Agency of Industrial Science and Technology in Japan under accession No. FERM-P 1,342) and known to be active against gram positive bacteria. The $LD_{50}$ values in mice of K-41 are 47.7 mg/kg (i.p.), 506.6 mg/kg (p.o.) and more than 1,000 mg/kg (s.c.), respectively. The physicochemical properties of the antibiotic K-41 and the process for its preparation are shown in Japanese Patent Specification Open to Public Inspection No. 14,692/1974 and in the Journal of Antibiotics Vol. 29, No. 1, pp 10–14 (1976). The present inventor has discovered that the said antibiotic K-41 has miticidal activity.

The process for preparing antibiotic K-41 is disclosed in the above-mentioned Journal of Antibiotics as follows:

Production: Streptomyces K-41 was inoculated into 100 ml of a medium composed of Bacto-Soytone (DIFCO) 1.0%, soluble starch 2.0%, glycerin 0.5%, corn steep liquor 0.5%, NaCl 0.35%, glucose 0.3% (pH adjusted to 6.6), and $CaCO_3$ 0.5%, in a 500-ml Sakaguchi flask and cultured at 28° C. for 4 days on a reciprocal shaker.

Isolation and purification: About 2.5 liters of the culture broth was filtered using filter-aid. The wet mycelial cake was stirred in 500 ml of ethyl acetate for 30 minutes, and the mixture was filtered. The ethyl acetate layer was evaporated in vacuo to give 1.0 g of crude product. The culture filtrate was extracted with ethyl acetate (500 ml×2), and the evaporation of the solvent gave 0.8 g of crude product. The crude products were combined and fractionated on a silica gel column (40 g) with a solvent system of $CHCl_3$—$CH_3OH$ ($CH_3OH$ 0~2%) to give 750 mg of active fraction, which was further purified by preparative TLC on silica gel with $CHCl_3$—$CH_3OH$ (95:5). The mixed salts (520 mg) were dissolved in $CHCl_3$ and shaken with 2% tartaric acid, and the $CHCl_3$-layer was treated with 5% $Na_2CO_3$, dried over $Na_2SO_4$ and evaporated. The residue was crystallized with petroleum ether to afford 248 mg of pure sodium salt in colorless prisms, m.p. 196°~198° C. (decomp.), $[\alpha]_D^{23} + 1.9 \pm 0.4°$ (c 1.017, MeOH).

Anal. Calcd. for $C_{48}H_{81}O_{19}Na$: C, 58.52; H, 8.29; Na, 2.33; 5MeO**, 15.75%. Found: C, 58.62; H, 8.33; Na, 2.28; MeO, 16.61%.

(** The presence of five methoxyl groups is confirmed by PMR and $^{13}C$ NMR spectra.)

The sodium salt readily gave the free acid as a colorless amorphous powder, but K-41 is less stable in acid form.

A basic object of this invention is to provide novel miticidal compositions containing an effective amount of antibiotic K-41 in combination with suitable carriers and other ingredients, if necessary. A further object of this invention is to provide a process for preparing the said compositions and a method to protect plants and animals from attack of various mites including adults and larvae.

The compositions of this invention are well suited for control of a variety of mites including Family Tetranychidae, for example, *Tetranychus cinnabarinus, Panonychus citri, Panonychus ulmi, Eotetranychus sexmaculatus Eotetranychus kankitus, tetranychus viennensis, Tetranychus urticae, Bryobia praetiosa, Bryobia rubrioculus, Eotetranychus smithi, Tetranychus kanzawai, Tetranychus desertorum;* Family Tenuipalpidae, for example, *Brevipaltus lewisi, Tenuipalpus zhizhilashviliae;* Family Eriophyidae, for example, *Aculus pelekassi, Calepitrimerus vitis;* Family Acaridae, for example, *Rhiizoglyphus echinopus;* Family Ixodidae; Family Pyroglyphidae and the like.

In addition, the compositions of this invention have demonstrated a high grade of activity against various strains resistant to other miticides.

The active ingredient, antibiotic K-41, may be used in the form of metal salts, i.e. sodium, potassium, calcium, magnesium, and iron salts. Ammonium salt is also acceptable. The antibiotic K-41 and the salts may be used singly or as a mixture, if desired.

The miticidal compositions of this invention may be prepared in various conventional forms such as aerosols, solutions, emulsions, emulsifiable concentrates, wettable powders, pastes, dusts, pellets, tablets and the like according to the manner of use intended. The compositions may normally contain from about 0.01 percent by weight to about 90 percent by weight of the antibiotic K-41 as the active ingredient, the amount depending on the form of compositions as well as the manner of use intended. To formulate the compositions, suitable gaseous, liquid, or solid carriers and other ingredients including surface active agents are used in addition to the antibiotic K-41, and conventional techniques for mixing, blending, crushing, granulating, or tableting may optionally be adopted. In addition to surface active agents, other adjuvants such as spreaders, synergists and other agents for preparing agricultural compositions may be used, if desired.

The surface active agents used in preparing the compositions of the invention can be wetting, dispersing, or emulsifying agents. They may act, for example, as wetting agents for wettable powders and dusts, as dispersing agents for wettable powders and suspensions and as emulsifying agents for emulsions and emulsifiable concentrates. Suitable surface active agents for use in the compositions may be anionic, non-ionic or cationic surface active agents. Such surface active agents are well known and reference may be made to U.S. Pat. No. 2,547,724, columns 3 and 4. For example, such surface active agents include polyethylene glycol esters with fatty acids; polyethylene glycol ethers with alkyl phenols or with long-chain aliphatic alcohols; polyethylene glycol ethers with sorbitan fatty acid esters; polyoxyethylenethio ethers; polyoxyethylenealkylaryl ethers; ammonium, alkali or alkaline earth salts of alkylaryl sulfonic acids; ammonium, alkali, or alkaline earth fatty alcohol sulfates; fatty acid esters of ammonium, alkali or alkaline earth isothionates or taurates; ammonium, alkali, or alkaline earth salts of lignin sulfonic acids; methylated or hydroxyethylated cellulose; polyvinyl alcohols; alkylsubstituted polyvinyl pyrrolidones; ammonium, alkali, or alkaline earth salts of polymerized alkylnaphthalene sulfonic acids; and long-chain quaternary ammonium compounds. Surface active agents may enhance the biological activity of the active ingredient antibiotic K-41.

Examples of the gaseous carrier include butane, nitrogen, carbon dioxide, Freon, and other inert gases. Liquid carriers for the present compositions may be water, or suitable inert organic solvents such as aliphatic hydrocarbons (e.g. pentane, hexane, cyclohexane, petroleum ether, gasoline, kerosene), aromatic hydrocarbons (e.g. benzene, toluene, xylene, naphtha), halogenated hydrocarbons (e.g. methylene chloride, chloroform, carbon tetrachloride, trichloroethane), ketones (e.g. acetone, methyl ethyl ketone, cyclohexanone), ethers (e.g. ether, isopropyl ether, tetrahydrofuran, dioxane), esters (e.g. ethyl acetate, amyl acetate) or alcohols (e.g. methanol, ethanol, butanol). Solid carriers may be, for example, mineral powders (e.g. clay, talc, mica, kaolin, bentonite, pyrophyllite, diatomaceous earth, silica gel), vegetable powders (e.g. soybean powder, wheat powder) or other powders conventionally used as agricultural solid carriers or diluents.

More particularly, preferred forms of the compositions of the invention for use may be solutions, emulsions, emulsifiable concentrates, wettable powders or dusts.

The antibiotic K-41 uniformly admixed with surface active agents may be dissolved in a suitable solvent to prepare an emulsifiable concentrate. The antibiotic K-41 may be uniformly admixed with a surface active agent as a dispersing agent and a carrier, subsequently ground to prepare a fine composition as wettable powder. The antibiotic K-41 and a suitable carrier such as a fine mineral powder are blended to a uniform mixture of dust.

For plants, the compositions of this invention may contain, in addition to the antibiotic K-41, other miticides, plant-regulants, plant-hormones, germicides, insecticides, fungicides, nematocides, herbicides, fertilizers and the like. Medicines for external use may be combined with the compositions for animals.

The process for preparing the miticidal compositions for plants is shown by means of, for example, an emulsifiable concentrate, a wettable powder and a dust as follows:

(1) Mixing 25–55 parts of the antibiotic K-41 and 5 to 15 parts of a surface active agent in 40 to 60 parts of an organic solvent with stirring in a vessel at a temperature of 5° to 40° C. under a relative humidity of 30 to 70% and filtering the homogenous mixture through a filter paper precoated to a thickness of 10 mm or less after addition of 1% filter aid to give a clear emulsifiable concentrate, (2) dissolving 10–60 parts of the antibiotic K-41 in 5 to 20 parts of an organic solvent, homogeneously mixing the solution with 30 to 60 parts of a mineral powder and 5 to 10 parts of an adjuvant in a powder-liquid mixer and grinding the mixture, so that more than 90% particles are 44μ or less in diameter, in a hummer mill or a jet mill to give a wettable powder; the entire procedure being effected at a temperature of 5° to 40° C. under a relative humidity of 30 to 70%, and (3) dissolving 1 to 27 parts of the antibiotic K-41 in 3 to 20 parts of an organic solvent and homogeneously grinding the solution with 70 to 90 parts of a mineral powder and 3 to 10 parts of an adjuvant to give a dust; the entire procedure being effected at a temperature of 5° to 40° C. under a relative humidity of 30 to 70%. The above processes are solely examples. The conditions can be changed to those usually used to prepare this type of composition. The proportion of the ingredients is also changeable.

The various formulations of the compositions of the invention described above can be applied by suitable means well known in the art. Methods and rates of application will be determined in accordance with the intended use and are, of course, influenced by the species of mites to be controlled, their stage in the life cycle, the manner of treatment, and the weather conditions prevalent during the application.

The compositions may be applied to soil, leaves, fruit, trees, flowers, poultry houses, domestic animals and the like by spraying or other means.

The rate of application may be expressed in several different ways. Ordinarily for crops growing in the field it is customary and convenient to express dosages in terms of weight per unit of field area treated. The total active ingredient amount employed for the compositions of the invention will usually range from 0.01 to 10 kilograms per hectare. However, for convenience and economy, the rate will ordinarily range from 0.05 to 2 kilograms per hectare and preferably from 0.1 to 1 kilogram per hectare, of the active ingredient.

Another manner of expressing the rate of application of the compositions of the invention is the unit of weight of active ingredient per given volume of water in the resulting solution, suspension or emulsion when used to spray the mite to be controlled or the locus thereof. Expressed in these terms, the total amount of the active ingredient in the compositions ranges from 1 to 1000 grams per 1000 liters of water. For reasons of economy and convenience, the range will ordinarily be from 1 to 500 grams per 1000 liters of water, more preferably 1 to 200 grams per 1000 liters of water.

To ensure the miticidal effect, it may be recommended that the treatment is repeated 2 or 3 times in a few days or over a 1- or 2-week periods, though the full effect can usually be obtained by a single treatment.

The compositions may be applied in a similar manner to control animal mites.

Some test data are shown below to illustrate the miticidal effects of the present compositions.

EXPERIMENT 1

Effect on adults of *Tetranychus cinnabarinus* and *Tetranychus urticae*

(1) Test Method: A leaf disc (2 cm in diameter) of Kidney bean (kind: Masterpiece) placed on wet filter paper was infected with about 15 adults of *Tetranychus cinnabarinus* (or *Tetranychus urticae*) and kept at 25° C. overnight. After dead and weak adults were removed, an aqueous solution (2 ml) containing K-41 at a pre-determined concentration prepared by the method described below was applied on the leaf with a sprayer. The discs were kept at 25° C. and the numbers of dead adults were counted after 24 and 48 hours.

The results are shown in Tables 1 and 2.

(2) Preparation of Test Solutions: Precisely weighed 100 mg of K-41 was dissolved in dimethylformamide (1-2 ml). To the solution is added Tween 20 (100 mg) with enough stirring. Distilled water is added to the solution to get the desired concentration.

Table 1:

| Effect on Adults of *Tetranychus cinnabarinus* | | | |
|---|---|---|---|
| Concentration of K-41 (ppm) | Number of Test Adults | Adulticidal Rate (%) 24 hr | 48 hr |
| 250 | 54 | 98.1 | 100 |
| 125 | 56 | 76.8 | 85.2 |
| 62.5 | 47 | 61.7 | 68.9 |
| 0 | 70 | 1.4 | 3.1 |

Table 2:

| Effect on Adults of *Tetranychus urticae* | | | |
|---|---|---|---|
| Concentration of K-41 (ppm) | Number of Test Adults | Adulticidal Rate (%) 24 hr | 48 hr |
| 250 | 46 | 97.8 | 100 |
| 125 | 48 | 91.7 | 95.7 |
| 62.5 | 54 | 46.3 | 48.1 |
| 0 | 61 | 3.3 | 3.3 |

EXPERIMENT 2

Effect on adults of *Panonychus citri*

(1) Test Method: A leaf from a lemon tree was placed on a 0.25% agar medium and was infected with about 13 adults of *Panonychus citri* and kept at 25° C. overnight. After removal of dead and weak adults, an aqueous solution (2 ml) containing K-41 at a predetermined concentration prepared in the same manner as shown in Experiment 1 was applied to the leaf disc with a sprayer. The leaf discs were at 25° C. and the numbers of dead adults were counted after 24 and 48 hours.

The results are shown in Table 3.

Table 3:

| Effect on Adults of *Panocychus citri* | | | |
|---|---|---|---|
| Concentration of K-41 (ppm) | Number of Test Adults | Adulticidal Rate (%) 24 hr | 48 hr |
| 250 | 46 | 97.8 | 100 |
| 125 | 45 | 86.7 | 95.5 |
| 62.5 | 41 | 48.8 | 64.9 |
| 0 | 56 | 1.8 | 3.6 |

EXPERIMENT 3

Effect on adults of *Tetranychus urticae*

(1) Test Method: all leaves except the first leaves were removed from a young Kidney bean plant of 10 days after sowing in a pot (9 cm in diameter). Then 30 adults of *Tetranychus urticae* each were placed on both the first leaves (total 60 adults of *Tetranychus urticae*). The pot was kept in a green house overnight. A solution containing K-41 at a pre-determined concentration prepared in the same manner as described in Experiment 1 is sprayed onto two sides of the leaves with 10 ml/pot using a glass spray. The test was effected in duplicate for a single test solution of a fixed concentration. The test plants were kept at 20° to 30° C. in a green house for ten days and then the numbers of living adults and larvae on the leaves were counted, observing the damage to the leaves caused by mites.

The results are shown in Table 4.

Table 4:

| Effect on Adults of *Tetranychus urticae* | | | | | |
|---|---|---|---|---|---|
| Concentration of K-41 (ppm) | Leaf No. | Number of Adults | Number of Larvae | Total | Damage* to Leaf |
| 125 | I | 0 | 0 | 0 | — |
| | II | 0 | 0 | 0 | — |
| | III | 0 | 0 | 0 | — |
| | IV | 0 | 0 | 0 | — |
| | Total | 0 | 0 | 0 | |
| 62.5 | I | 0 | 0 | 0 | — |
| | II | 1 | 0 | 1 | — |
| | III | 0 | 0 | 0 | — |
| | IV | 0 | 0 | 0 | — |
| | Total | 1 | 0 | 1 | |
| 0 | I | 94 | 312 | 406 | +++ |
| | II | 92 | 298 | 390 | +++ |
| | III | 82 | 397 | 479 | +++ |
| | IV | 98 | 291 | 389 | +++ |
| | Total | 366 | 1298 | 1664 | |

*The damage to the leaf was judged by the degree of chlorosis.
— No change was recognized compared with the state when sprayed.
+++ Whole leaf was damaged and almost withered.

The following examples are given solely for the purpose of illustration and are not to be construed as limiting this invention, many variation of which are possible.

EXAMPLE 1

An emulsifiable concentrate of the following composition is prepared:

| K-41 | 10% by weight |
|---|---|
| Xylene | 40% by weight |

Polyoxyethylenealkylaryl ether 50% by weight The above ingredients are mixed and blended homogeneously. The emulsifiable concentrate is diluted 400- to 1000-fold with water before application.

EXAMPLE 2

An emulsifiable concentrate of the following composition is prepared:

| K-41 sodium salt | 10% by weight |
|---|---|
| Xylene | 50% by weight |
| Dimethylformamide | 30% by weight |
| Polyoxyethylenealkylaryl ether | 10% by weight |

The emulsifiable concentrate is diluted 400- to 2000-fold with water before application.

EXAMPLE 3

A solution of the following composition is prepared:

| K-41 | 3% by weight |
|---|---|
| Cyclohexanone | 77% by weight |
| Polyoxyethylenealkylaryl ether | 20% by weight |

The solution is diluted to 100- to 500-fold with water before application.

EXAMPLE 4

A wettable powder of the following composition is prepared:

| K-41 | 15% by weight |
|---|---|
| Diatomaceous earth | 80% by weight |
| Sodium lignin sulfonate | 2% by weight |

-continued

| Sodium alkylbenzene sulfonate | 3% by weight |

The ingredients are mixed homogeneously and ground to fine powder. The wettable powder is diluted to 500- to 1500-fold with water before application.

EXAMPLE 5

A wettable powder of the following composition is prepared:

| K-41 potassium salt | 10% by weight |
| White carbon | 15% by weight |
| Clay | 40% by weight |
| Diatomaceous earth | 30% by weight |
| Sodium alkylbenzene sulfonate | 2% by weight |
| Sodium lignin sulfonate | 3% by weight |

The wettable powder is diluted with water before application.

EXAMPLE 6

A wettable powder of the following composition is prepared:

| K-41 | 50% by weight |
| Sodium lignin sulfonate | 5% by weight |
| Sodium alkylbenzene sulfonate | 3% by weight |
| Clay | 42% by weight |

The wettable powder is diluted with water before application.

EXAMPLE 7

A wettable powder of the following composition is prepared:

| K-41 | 20% by weight |
| Diatomaceous earth | 30% by weight |
| Kaolin | 42% by weight |
| A mixture of sodium lauryl sulfonate and sodium | |
| dinaphthylmethane disulfate | 8% by weight |

The ingredient are mixed homogeneously and ground to fine powder. The wettable powder is diluted with water before application.

EXAMPLE 8

A dust of the following composition is prepared:

| K-41 | 3% by weight |
| Talc | 97% by weight |

The ingredients are mixed homogeneously and ground to fine powder.

EXAMPLE 9

A mixture of the following composition is prepared:

| K-41 sodium salt | 5% by weight |
| Sodium dodecylbenzenesulfonate | 2% by weight |
| Clay | 38% by weight |
| Bentonite powder | 55% by weight |

After blending, the mixture is kneaded with water, granulated, and dried to obtain granules.

What is claimed is:

1. A method for controlling mites which attack plants, which comprises applying to the miles a miticidal amount of a composition containing a miticidal amount of K-41 or a miticidal salt thereof, as an active ingredient, and a carrier therefor.

2. A method according to claim 1, wherein the composition contains from about 0.01 to about 90% by weight of K-41 or a miticidal salt thereof.

3. A method according to claim 1, wherein the plants are fruit trees.

4. A method according to claim 1, wherein the plants are vegetable plants.

5. A method according to claim 1, wherein the plants are flowering horticultural plants.

* * * * *